(12) United States Patent
Boehm et al.

(10) Patent No.: US 9,775,951 B2
(45) Date of Patent: Oct. 3, 2017

(54) PLUNGER FOR A SYRINGE AND METHOD OF MAKING SUCH A PLUNGER

(75) Inventors: Andreas J. Boehm, Reichling (DE); Alexander Walter, Pürgen (DE)

(73) Assignee: 3M Innovative Properties Company, St. Paul, MN (US)

( * ) Notice: Subject to any disclaimer, the term of this patent is extended or adjusted under 35 U.S.C. 154(b) by 271 days.

(21) Appl. No.: 13/407,189

(22) Filed: Feb. 28, 2012

(65) Prior Publication Data

US 2012/0225405 A1 Sep. 6, 2012

(30) Foreign Application Priority Data

Mar. 4, 2011 (EP) .................................... 11156905

(51) Int. Cl.
- *A61M 5/315* (2006.01)
- *A61C 9/00* (2006.01)
- *A61C 5/62* (2017.01)

(52) U.S. Cl.
CPC ........... *A61M 5/31513* (2013.01); *A61C 5/62* (2017.02); *A61C 9/0026* (2013.01)

(58) Field of Classification Search
CPC .... A61M 2005/31506; A61M 5/31513; A61C 5/062; A61C 9/0026; A61C 5/62
USPC .......... 433/80, 89, 90; 264/328.12; 222/326, 222/386; 604/218, 222, 228, 230
See application file for complete search history.

(56) References Cited

U.S. PATENT DOCUMENTS

| | | |
|---|---|---|
| 3,674,181 A | 7/1972 | Marks |
| 3,729,032 A | 4/1973 | Tischlinger |
| 4,492,576 A | 1/1985 | Dragan |
| 4,543,093 A | 9/1985 | Christinger |
| 4,952,209 A * | 8/1990 | Muhlbauer ................... 604/218 |
| 5,460,523 A | 10/1995 | Schulman |
| 5,735,437 A * | 4/1998 | Broyles et al. ............... 222/137 |
| 5,848,894 A * | 12/1998 | Rogers ............................ 433/90 |
| 5,911,715 A * | 6/1999 | Berg ................. A61M 25/0009 138/125 |
| 6,270,562 B1 * | 8/2001 | Jia ................................... 106/35 |
| 6,287,122 B1 * | 9/2001 | Seeram .................. A61C 5/007 433/220 |
| 6,447,866 B1 * | 9/2002 | Kagan et al. .................... 428/58 |
| 6,503,084 B2 * | 1/2003 | Evers et al. .................. 433/226 |
| 6,740,062 B2 | 5/2004 | Hjertman |
| 6,805,686 B1 * | 10/2004 | Fathallah ............ A61M 5/2033 604/134 |
| 7,087,037 B2 * | 8/2006 | Chiba et al. .................... 604/38 |

(Continued)

FOREIGN PATENT DOCUMENTS

| | | |
|---|---|---|
| EP | 0372549 | 6/1990 |
| WO | WO 2004/064901 | 8/2004 |
| WO | WO 2010/093575 | 8/2010 |

*Primary Examiner* — Edward Moran

(57) ABSTRACT

A plunger for advancing a substance in a syringe toward a dispensing nozzle. The plunger has a plunger rod and a seal and being formed of a plastic composition. The plastic composition includes a polymer and a filler which is non-uniformly distributed within the polymer to provide the plunger rod and the seal with different mechanical properties depending on the filler content in the portions of the plastic composition plunger forming the rod and the seal. The invention preferably provides a dental syringe which can be conveniently used, and further helps minimizing costs in the manufacturing of the dental syringe.

11 Claims, 4 Drawing Sheets

(56) References Cited

U.S. PATENT DOCUMENTS

| | | |
|---|---|---|
| 7,367,475 B2 | 5/2008 | Hörth |
| 2008/0050693 A1* | 2/2008 | Fischer et al. .................. 433/25 |
| 2008/0077086 A1* | 3/2008 | Lonien ................ A61M 5/5086 |
| | | 604/111 |
| 2009/0075226 A1* | 3/2009 | Oshida et al. ..................... 433/8 |
| 2010/0167231 A1* | 7/2010 | Dubbe .................. A61C 5/062 |
| | | 433/80 |
| 2012/0046411 A1* | 2/2012 | Kulshrestha ............ A61L 29/04 |
| | | 524/528 |

* cited by examiner

PLUNGER FOR A SYRINGE AND METHOD OF MAKING SUCH A PLUNGER

CROSS-REFERENCE TO RELATED APPLICATIONS

This application claims priority from European Patent Application Serial No. 11156905.9, filed Mar. 4, 2011, the disclosure of which is incorporated by reference in its entirety herein.

FIELD OF THE INVENTION

The invention relates to a plunger for a syringe, wherein the plunger has a plunger rod and a seal. In particular the invention concerns a plunger that is formed of a plastic composition which comprises a polymer and a filler distributed therein, wherein the filler contents are different in the plunger rod and the seal. The invention further relates to a method of making such a plunger.

BACKGROUND ART

Some dental substances are provided in a syringe for application directly in a patient's mouth. There are syringes which are configured to store a readily usable dental substance, and further syringes which are configured to store individual components of a dental substance which are to be mixed together only shortly before use.

For example WO 2010/093575 discloses a syringe for dispensing a multi-component material. The syringe comprises a syringe cartridge having compartments for components of the multi-component material and a static mixer connected to the cartridge. The syringe further has a plunger assembly that is movable into the syringe cartridge to dispense material from the syringe.

Although there are a variety of syringes for dental use there is still a need for a syringe that is relatively reliable in use, and nevertheless relatively inexpensive. Such a syringe is desirably easy and convenient to use.

SUMMARY OF THE INVENTION

In one aspect the invention relates to a plunger for advancing a substance in a syringe toward a dispensing nozzle. The plunger has a plunger rod and a seal for sealing the plunger and the syringe relative to each other. Further the plunger is formed of a plastic composition which comprises a polymer and a filler distributed within the polymer. In particular the filler is distributed with a first relative filler content by weight in the plunger rod and a second relative filler content by weight in the seal, and wherein the first filler content is higher than the second filler content.

Therefore the filler is preferably non-uniformly distributed within the plastic composition such that the plastic composition comprises at least a first portion having a higher filler content relative to at least a second portion of the same plastic composition. The first portion of the quantity of a plastic composition may form the plunger rod, whereas the second portion of the quantity of a plastic composition may form the seal. Thus the plunger rod and the seal preferably are provided with different mechanical properties. Such different properties preferably depend (or only depend) on the filler content in the first and second portions of the plastic composition.

The invention may be generally advantageous in that it may allow molding of a relatively mechanically stable part, but nevertheless provide the part with a portion having different mechanical properties, even though the same plastic composition is used for the entire part. In particular an elongated plunger may be provided with a certain resistance to buckling from axial load without or without substantially reinforcing the plunger by enlarged dimensions. Further the same plunger may be provided with a relatively soft and/or elastic seal without the use of a separate seal or a different plastic composition. The invention may further allow for molding a plunger having such portions of different mechanical properties in a single step. The invention be thus be advantageous in that it may help minimizing costs in the manufacturing of a dental syringe comprising the plunger of the invention. Further the invention may allow for the syringe to be designed relatively slim, for example like a pen. Therefore such syringe may be relatively convenient in use.

The relative filler content by weight (also referred to herein short as "filler content") is preferably determined by the weight of the filler relative to the weight of a quantity of the plastic composition including the filler. The relative filler content may be determined by:

providing a quantity of the plastic composition;
    determining the weight of the quantity of the plastic composition;
    firing the quantity of the plastic composition so as to burn the polymer but not the filler contained therein; and
    determining the weight of the residual filler which is not burned.

The weight of the residual filler divided by the weight of the quantity of the plastic composition for the purpose of this specification forms the filler content by weight.

The polymer preferably burns at a lower temperature than the filler so that selective burning of the polymer without burning the filler may easily achieved by adjusting the firing temperature accordingly.

In one embodiment the first filler content transitions gradually toward the second filler content. Thus the quantity of plastic composition forming both the plunger rod and the seal may have an average filler content which is non-uniformly distributed in the quantity of plastic composition such that different portions of the quantity of plastic composition have different filler contents, and wherein the different filler contents transition smoothly between one another.

In another embodiment the first filler content is between about 20% by weight and about 60% by weight. The first filler content may be an average filler content in the portion of the plastic composition forming the seal. Further the plastic composition may have an overall filler content of about 50%.

In one embodiment the plunger rod extends with a generally circular cross-section along a plunger axis, and the seal protrudes from the plunger rod circumferentially around the plunger axis. The seal therefore may be generally ring shaped, for example may form a radially outwardly extending lip seal, and extending circumferentially around the plunger rod. Further the seal may be generally funnel shaped, for example may form a conically extending lip seal, and extending circumferentially around an end of the plunger rod. The skilled person will recognize other shapes and types which may be likewise used with the present invention. Further the skilled person will be able to use one or more seals of the same seal or a combination of different seals.

In one embodiment the plunger axis extends generally linear. Such a plunger may be used with a generally straight syringe. Alternatively the plunger axis may extend along a curve which resembles at least a section of a circle. Such a plunger may be used with a curved syringe.

In a further embodiment the plunger rod comprises an annular groove about the plunger axis with the seal protruding from the plunger rod in an area of the groove. Therefore the groove may provide for additional space for the seal. The seal thus may protrude from the plunger rod toward a free end or edge of the seal at a certain maximized distance. Such distance may provide the seal with a maximized elasticity, and may allow for a maximized deformability of the seal.

In one embodiment the seal has an annular free edge and tapers from the piston rod toward the free edge. The edge may be relatively sharp but slightly rounded such that it can bend and conform to inner walls of a compartment in which the plunger rod may be inserted. Thus a relatively good seal between the plunger and the syringe may be formed.

In a further embodiment the plunger has a rear end which comprises a finger plate and an opposite front end comprising the seal. The seal may be arranged at the plunger rod adjacent the front end and the finger plate may form the rear end. The seal may substantially protrude in a plane that is arranged perpendicular to the plunger axis.

In one embodiment the polymer is a polyamide and the filler comprises glass or carbon fibers. The fibers may have an average length of between about 0.1 mm and 100, more preferably between about 0.1 mm and about 1 mm, or between about 1 mm and about 10 mm. The fibers may have an average diameter of about between 3 μm and about 13 μm, preferably about 10 μm.

In a further embodiment the plunger rod has a greatest diameter of about 3.61 mm. The plunger rod may have a length of between about 80 mm and 100 mm, preferably about 89.5 mm. The seal may have a greatest diameter of about 3.84 mm.

In one embodiment the plunger comprises at least two plunger rods each having a seal. The plunger may have a finger plate which connects the at least two plunger rods.

In one embodiment one of the plunger rods has a greatest diameter of about 3.95 mm and the other one of the plunger rods has a greatest diameter of about 2.75 mm. The plunger rods each may have a length of between about 80 mm and 100 mm, preferably about 89.5 mm. The seal of one of the plunger rods may have a greatest diameter of about 4.24 mm, and the seal of the other one of the plunger rods may have a greatest diameter of about 3.04 mm.

In one embodiment the plunger of the invention is comprised in a syringe for dispensing a substance. The syringe may have at least one compartment which contains at least a component of the dental substance. Further the syringe may have a dispensing nozzle which forms an outlet for the at least one component. The plunger may be slidably arranged within the compartment, and may be displaceable relative to the syringe in a direction toward the dispensing nozzle for advancing the component toward the dispensing nozzle. In a preferred embodiment the syringe has at least two compartments for receiving components of the substance to be dispensed. The at least two compartments may each contain a component of the dental substance. Further the syringe may have a plunger according to the invention. This plunger preferably comprises at least two plunger rods each having a seal. The plunger rods are preferably slidably and sealingly arranged within the respective compartments. Thus the plunger may be adapted to generally simultaneously advance the components toward the dispensing nozzle. The dispensing nozzle may further comprise a mixer for mixing the components as they flow through the dispensing nozzle.

In a further aspect the invention relates to a method of molding a plunger. The plunger of this method has a plunger rod and a seal. The method comprising the steps of:
  providing a molten plastic composition into a mold, wherein the mold comprises a first cavity for forming a seal and a second cavity for forming the plunger rod, the first and second cavities being connected for fluid communication and together forming one common cavity, the plastic composition comprising a polymer and a filler distributed within the polymer,
  causing a first portion of the plastic composition for forming the seal to reduce in filler content relative to the filler content in a second portion of the plastic composition, such that
  the filler is distributed with a first relative filler content by weight in the plunger rod and a second relative filler content by weight in the seal, wherein the first filler content is higher than the second filler content.

The filler content in the first portion of the plastic composition may be caused to reduce by forcing the molten plastic material into the first and second cavities, wherein the first cavity is smaller in size than the second cavity. In particular the first and second cavities preferably have first and second flow dimensions, respectively, which is a dimension parallel to a flow direction of the molten plastic composition for filling the mold. A flow direction is preferably determined in the mold by the position of a gate through which the molten plastic composition may be provided in the mold, and further by the shape of the cavity. In the example of the plunger of the invention the second flow dimension in the second cavity may be generally parallel to the plunger axis of the molded plunger, and the flow dimension in the first cavity may be arranged generally perpendicular thereto. Preferably the first and second cavities further have first and second flow cross-sections in a plane perpendicular to the first and second flow dimensions. The greatest first flow cross-section may be smaller than the smallest second cross section. Thus the first flow cross-section may form a constriction for the plastic composition flowing in the mold. This may cause the balance of the average filler content to be shifted from the plastic composition in the first cavity toward the plastic composition in the second cavity.

DETAILED DESCRIPTION OF THE INVENTION

Figure 1:
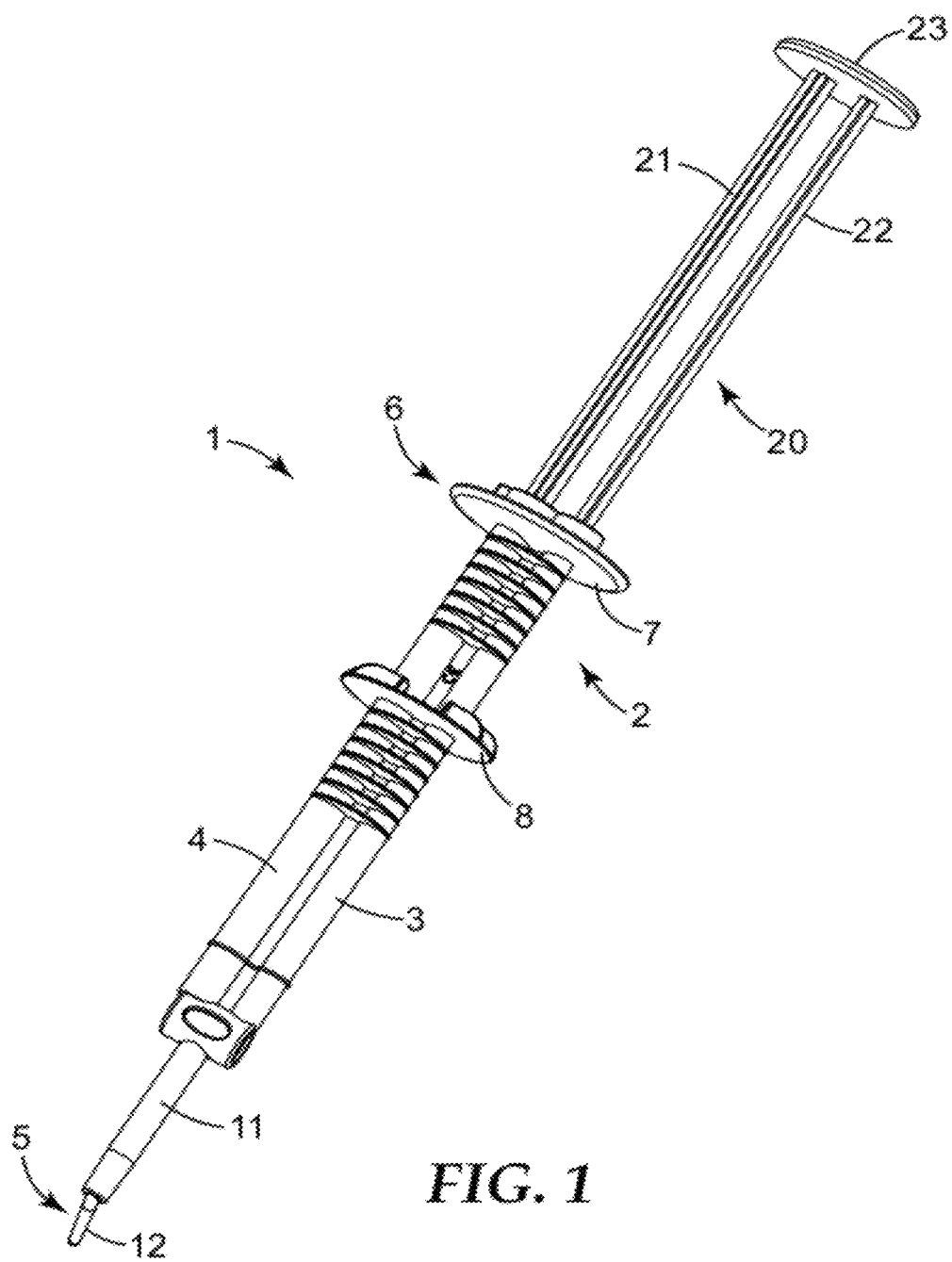
FIG. 1 is a perspective view of a syringe which comprises a plunger according to an embodiment of the invention.

FIG. 1 shows a syringe 1 for storing and dispensing a two-component dental substance. The syringe 1 comprises a cartridge 2 having two side-by-side compartments 3, 4. Each of the compartments may contain a component of the dental substance to be dispensed. The syringe 1 further has a mixing tip 11 adjacent a dispensing end 5. The mixing tip 11 forms an outlet 12 for the dental substance. A plunger 20 extends into the cartridge 2 at a rear end 6 of the cartridge 2. The plunger 20 comprises two plunger rods 21, 22 that are movably and sealingly arranged within the compartments 3, 4 respectively for advancing the components toward the dispensing end 5. By moving the plunger rods 21, 22 into the cartridge 2 the components thus may be extruded from the compartments 3, 4 and urged through the mixing tip 11 for mixing and for dispensing the dental substance mixed from the components. The mixing tip 11 may comprise a static mixer (not shown) for facilitating mixing of the components as the components flow through the mixing tip 11. The plunger rods 21, 22 are arranged on a common finger plate 23 at a rear end of the plunger 20. Thus the plunger rods 21, 22 are adapted to move simultaneously as the finger plate 23 is moved. Therefore the mixing ratio of the components essentially only depends on the inner cross-sections of the compartments 3, 4 in a plane perpendicular to a direction in which the plunger 20 is movable. In the example the compartment 4 has a larger inner-cross-section than the compartment 3 so that the mixing ratio between the components urged through the mixer is different from 1:1, for example 2:1. However the skilled person will recognize that the compartments 3, 4 may have equal or similar cross-sections to achieve a mixing ratio of the components of 1:1 or about 1:1. The dental substance may be a dental impression material, for example, which is prepared by help of the syringe from a mixture of a base component and a catalyst component.

The syringe 1 in the example is relatively long so that a sufficient amount of dental substance, for example impression material, may be made available. The syringe may be kept relatively slim so that it can be conveniently used in a patient's mouth. A convenient use may be further supported by several finger plates arranged at the cartridge 2.

The cartridge 2 in the example has two finger plates 7, 8 with a first finger plate 7 being located adjacent the rear end 6 of the cartridge 2, and s second finger plate 8 relative to the first finger plate 7 being arranged further toward the dispensing end 5 of the syringe 1. Thus in an initial stage in which the plunger 20 may be retracted from the cartridge 2 the syringe may be conveniently operated using the finger plate 23 of the plunger 20 and the first finger plate 7 of the cartridge 2. This is because the distance between the finger plate 23 of the plunger 20 and the first finger plate 7 of the cartridge 2 relative to each other may well suit the size of a user's hand. Once portions of the components are extruded from the compartments 3, 4 the plunger 20, and in particular the finger plate 23 may be positioned closer toward the cartridge 2. At this stage the syringe 1 may be more conveniently operated using the second finger plate 8 of the cartridge 2 with the finger plate 23 of the plunger 20. This is because the distance between the finger plate 23 of the plunger 20 and the first finger plate 7 of the cartridge 2 relative to each other may be quite short which may result in a reduced controllability relative to a longer distance between the finger plates.

Figure 2:
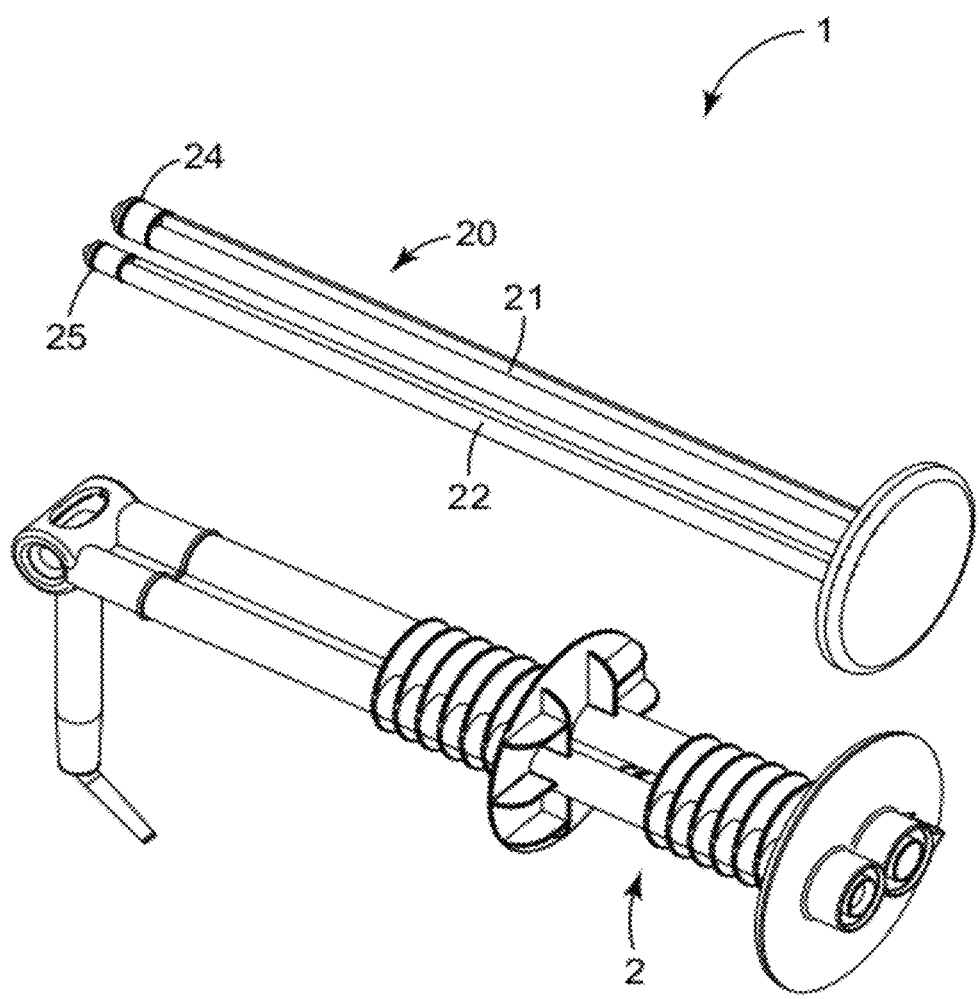
FIG. 2 is a perspective view of the syringe shown in FIG. 1 showing the syringe plunger in more detail.

FIG. 2 shows the syringe 1 with the cartridge 2 and the plunger 20 separated from each other. The plunger rods 21, 22 each have a seal 24, 25 respectively. The seals 24, 25 are formed in one piece (monolithically or integrally molded) with the plunger rods 21, 22. This avoids assembly of the seals on the plunger rods and therefore may help minimizing costs for manufacturing of the plunger 20. Further this preferably allows the plunger rods 21, 22 to be designed relatively tiny in cross-section because recesses for accommodating a separate seal may not be required. This is because recesses for seals may form weak areas with regard to the mechanical stability of the plunger rods, and the minimum dimensions of the plunger may have to be determined by the dimensions of the recesses if separate seals are used, whereas such limitations may not exist if seals formed in one piece with the plunger rods are used.

Figure 3:
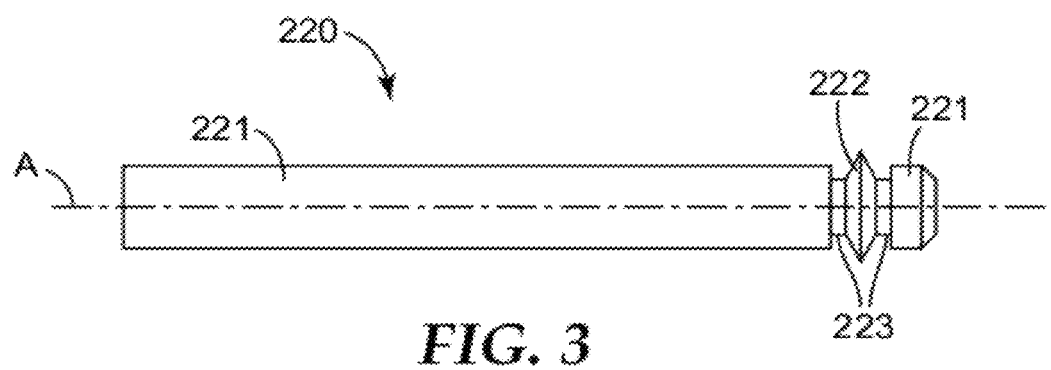
FIG. 3 is a side view of a plunger according to a further embodiment of the invention.

FIG. 3 shows a plunger 220 which has only one plunger rod 221 and a seal 222. The plunger rod 221 with the seal 222 may however form one of two or more plunger rods comprised in one plunger, and thus may technically correspond to one of the plunger rods 21/22 with seal 24/25 shown in FIG. 2. The plunger 220 overall is molded, preferably injection molded, of a plastic composition which comprises a polymer and a filler. For example the plunger 220 may be molded from a quantity of the plastic composition and the total quantity of the plastic composition may comprise an average filler content by weight. The filler is preferably distributed within the polymer. Further the filler is preferably selected for providing mechanical reinforcement within the plastic composition. Accordingly the filler may comprise glass fibers and/or carbon fibers or any other filler suitable to provide mechanical reinforcement within the plastic composition. The plunger rod 220 is formed of a first portion of the plastic composition which comprises the filler at a first filler content, and the seal 221 is formed of a second portion of the plastic composition which comprises the filler at a different second filler content. Therefore the first and second filler contents are different from the average filler content in the overall plunger. The different filler contents preferably result from a local displacement of filler from the second portion of the plastic composition toward the first portion of the plastic composition at a molten stage of the composition during molding of the plunger 220. Accordingly the first filler content is higher than the second filler content.

In the example the plunger has a plunger axis A along which the plunger rod 221 extends. The plunger rod 221 extends at least partially along the plunger axis A with a generally uniform cross-section. In the example the plunger rod 221 extends with a generally circular cross-section along the plunger axis A, and therefore forms a cylinder with the plunger axis A forming the cylinder axis. The seal 222 preferably circumferentially extends around the plunger rod 221. In particular the seal 222 protrudes from the plunger rod and tapers outwardly (in dimensions away from the plunger axis A) in a plane generally perpendicular on the plunger axis A. Thus the seal 222 is generally ring shaped and forms a generally circular outer sealing edge in a plane generally perpendicular on the plunger axis.

It has been found that the filler content within the seal decreases with the seal outwardly narrowing or tapering. Therefore the seal adjacent an outer periphery may be comprised of plastic composition having a lower filler content than the seal further inwardly. Further due to the filler content decreasing in the seal the overall filler content of the seal is preferably lower than the filler content of the plunger rod. Accordingly the seal adjacent an outer periphery may have a modulus of elasticity which is lower than a modulus of elasticity of the seal further inwardly. This is advantageous because this preferably allows a plunger to be made of a plastic composition which is suitable to provide a relatively rigid plunger rod whereas the same composition may be used to make a relatively soft or elastic seal.

Therefore the plunger of the invention may be relatively resistant to an axial buckling load applied to it, but also may form a good seal in use with a syringe. Further such plunger may help minimizing costs in manufacturing of the plunger because additional assembly steps for a seal may be omitted.

It has further been found that a minimized content of fillers in the seal may help minimizing wear of the syringe because only a minimized amount of fillers may be exposed at an outer surface of the seal. Thus abrasion caused by the fillers sliding on a surface of the syringe (for example fibers sticking out of the sealing edge and sliding on a wall surface of a compartment) may be minimized, and accordingly a syringe used with the plunger of the invention may operate more reliably over a longer time.

The skilled person will recognize that other shapes and arrangements of the seal relative to the plunger rod may be likewise used as long as the seal comprises a portion which is narrowed (for example tapered toward a relatively sharp outward edge) with respect to other portions of the plunger or seal.

The plunger 220 in the example has a groove shaped recess 223 within the plunger rod 221. The recess extends circumferentially within plunger rod 221 and the seal 221 protrudes from a surface in the recess. While the recess is optional it may allow maximizing the radial dimension of the seal relative to the plunger axis. Therefore the elasticity of the seal may be further maximized.

Figure 4:
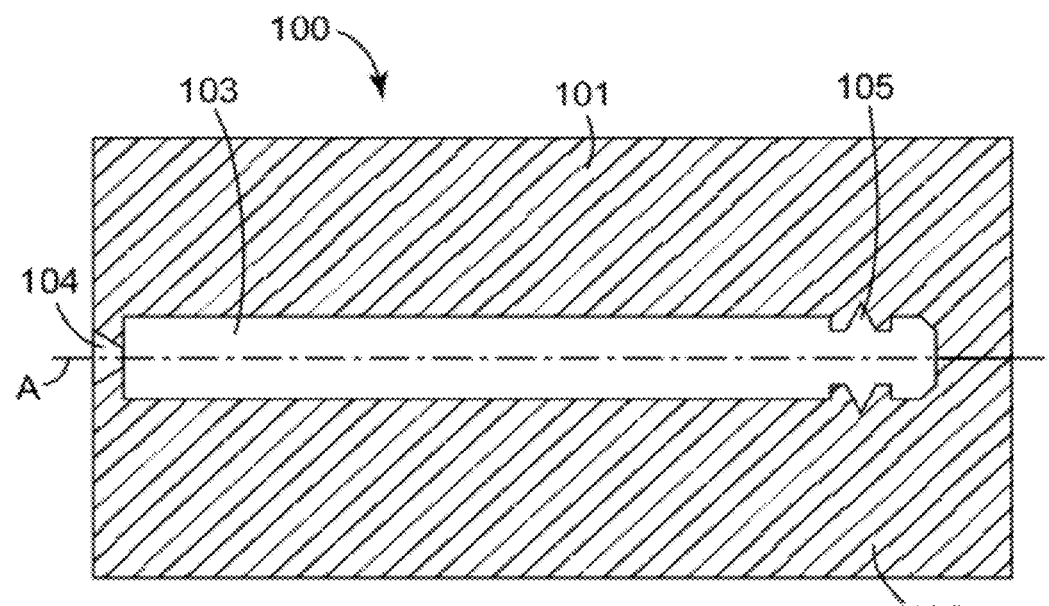
FIG. 4 is a cross-sectional view of a mold for making a plunger according to an embodiment of the invention.

FIG. 4 shows a mold 100 which has two separable mold parts 101, 102. The mold parts 101, 102 in combination form a mold cavity 103 which generally corresponds in shape to a negative shape of the plunger shown in FIG. 3. The mold 100 may be used with an injection molding machine (not shown). The plunger may be made by providing a flowable plastic composition which comprises a molten hardenable polymer and dispersed therein a filler. The flowable plastic composition may be provided into the mold 100 via gate 104 which is arranged adjacent a rear end of the finished plunger rod. The flowable plastic composition may be caused to flow along plunger axis A toward an opposite front end of the finished plunger rod. Thereby the flowable plastic composition may be also caused to flow laterally to the plunger axis A into an annular partial cavity 105 which is shaped to form the seal of the plunger. The plastic composition may be caused to harden (for example by cooling) before the mold is separated to eject the molded plunger. Thus the plunger and the seal may be molded in one single molding step and form a single contiguous plastic composition, however the molded plunger and seal may exhibit different properties resulting from different filler contents in the hardened plastic composition.

Figure 5:
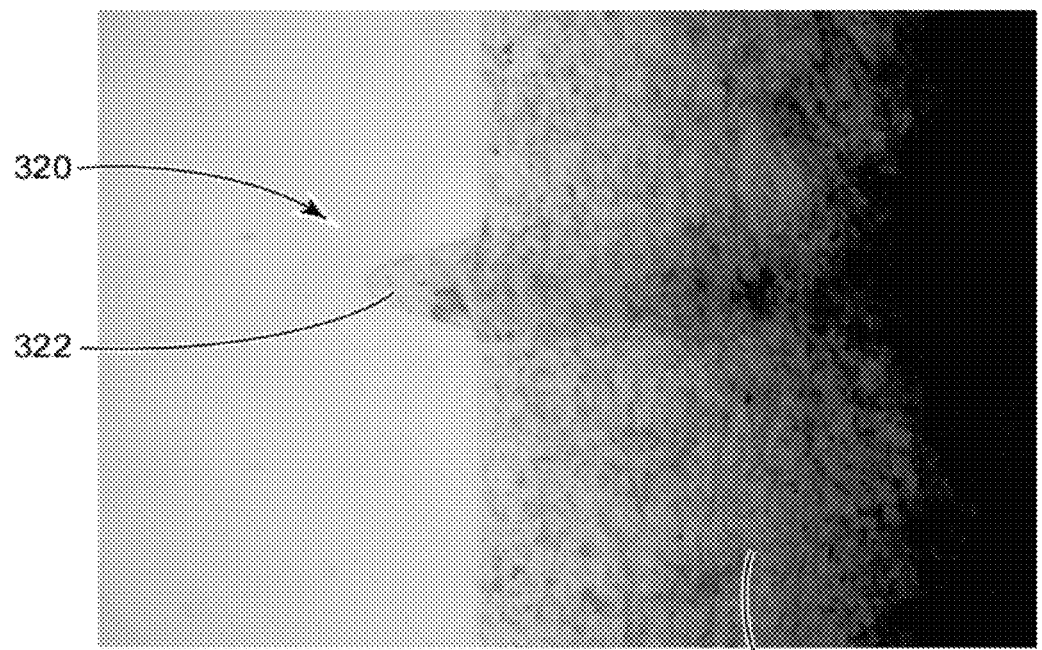
FIG. 5 is a photo of a cut of a plunger according to an embodiment of the invention.

FIG. 5 is a photo of a portion of a plunger 320 according to the invention. The plastic composition comprises a filler, and in particular glass fibers that are visible as dark spots or lines in the photograph. As apparent from the photo the plunger 320 has a seal 322 which comprises a lower content of glass fibers than portions 321 of a plunger rod of the plunger 320. Accordingly the seal 322 has a lower modulus of elasticity than the plunger rod 321.

Figure 6:
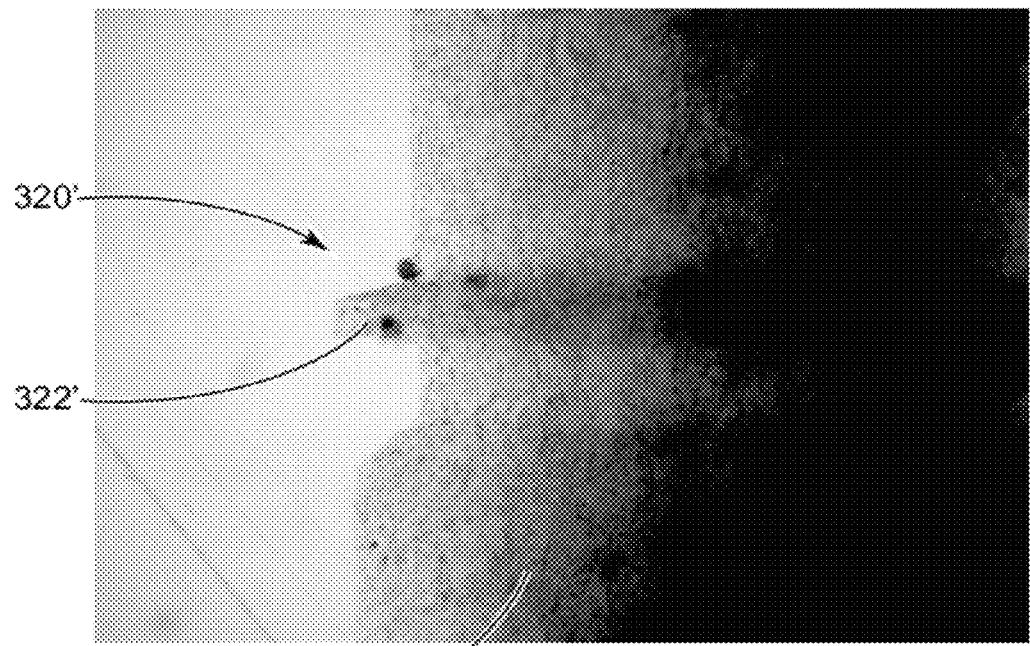
FIG. 6 is a photo of a cut of a plunger according to another embodiment of the invention.

FIG. 6 is a photo of a portion of a plunger 320' after insertion in a compartment of a syringe. The Plunger 320' has a seal 322' which prior to insertion in the compartment had an outer diameter which was greater than an inner diameter of the compartment. Accordingly the seal 322' was squeezed from insertion in the compartment. The seal 322' was partially plastically and partially elastically deformed. Thus a good seal was achieved between the plunger 320' and the compartment because the seal was enabled to conform to the compartment.

The invention claimed is:

1. A plunger for advancing a substance in a syringe toward a dispensing nozzle, the plunger having a plunger rod with an annular groove extending circumferentially within the plunger rod between a first end and a second end of the plunger rod, and a seal for sealing the plunger and the syringe relative to each other, where the seal protrudes from the annular groove to provide a surface of the annular groove on either side of the seal and wherein the seal has an annular free edge and tapers from the plunger rod toward the free edge, where the plunger rod and the seal are monolithically molded in one common cavity of a mold from a total quantity of a plastic composition that includes a polymer and a filler distributed in the polymer to form the plunger as one piece, where the plunger rod includes the filler at a first filler content by weight and the seal includes the filler at a second relative filler content by weight, where the first filler content is higher than the second filler content so that the plunger rod and the seal are provided with different mechanical properties, where the first filler content transitions gradually toward the second filler content with the seal outwardly narrowing such that the seal adjacent an outer periphery has a lower filler content than the seal adjacent the plunger rod.

2. The plunger of claim 1, wherein the total quantity of the plastic composition used to form the plunger rod and the seal has an overall filler content of 50% by weight.

3. The plunger of claim 1, wherein the plunger rod extends with a generally circular cross-section along a plunger axis, and wherein the seal protrudes from the plunger rod circumferentially around the plunger axis.

4. The plunger of claim 3, wherein the plunger axis extends generally linear.

5. The plunger of claim 1, wherein the plunger has a rear end which comprises a finger plate and an opposite front end comprising the seal.

6. The plunger of any of the claim 3, wherein the seal substantially protrudes in a plane that is arranged perpendicular to the plunger axis.

7. The plunger of claim 3, wherein the polymer is a polyamide and the filler comprises glass or carbon fibers.

8. The plunger of claim 7, wherein the fibers have an average length of 0.2 mm and a diameter of 10 μm.

9. The plunger of claim 1, where the plunger includes at least two of the plunger rods each having one of the seals.

10. A syringe for dispensing a substance, comprising a plunger of claim 1.

11. The plunger of claim 1, where the plunger rod longitudinally extends on either side of the outer periphery of the seal.

* * * * *